US005482970A

United States Patent [19]

Kim et al.

[11] Patent Number: 5,482,970

[45] Date of Patent: Jan. 9, 1996

[54] TRANSDERMAL ANTIANDROGENIC COMPOSITIONS AND MODULATED PROCESS

[75] Inventors: Kwon H. Kim, Bridgewater; Barry Koplowitz, Somerville; Norman L. Henderson, Gladstone, all of N.J.

[73] Assignee: Hoechst-Roussel Pharmaceuticals Inc., Somerville, N.J.

[21] Appl. No.: 123,412

[22] Filed: Sep. 17, 1993

Related U.S. Application Data

[63] Continuation of Ser. No. 859,745, Mar. 30, 1992, abandoned.

[51] Int. Cl.$^6$ .................................................. A01N 37/10

[52] U.S. Cl. .......................... 514/532; 514/691; 514/944; 514/946; 514/947; 514/969; 424/443; 424/446

[58] Field of Search .................................... 424/448, 443; 514/944, 946, 350, 691, 532

[56] References Cited

U.S. PATENT DOCUMENTS

| | | | |
|---|---|---|---|
| 3,472,931 | 10/1969 | Stoughton | 424/180 |
| 3,551,554 | 12/1970 | Herschler | 424/7 |
| 3,969,516 | 7/1976 | Stoughton | 424/181 |
| 3,989,816 | 11/1976 | Rajadhyaksha | 424/60 |
| 4,017,641 | 4/1977 | DiGiulio | 424/365 |
| 4,202,888 | 5/1980 | Eckert | 424/182 |
| 4,466,971 | 8/1984 | Bouton | 424/266 |
| 4,684,635 | 8/1987 | Orentreich | 514/170 |
| 4,783,450 | 11/1988 | Fawzi | 514/78 |
| 4,788,062 | 11/1988 | Gale | 424/449 |
| 4,788,063 | 11/1988 | Fisher | 424/449 |
| 4,804,541 | 2/1989 | Nichols | 424/449 |
| 4,808,414 | 2/1989 | Peck | 424/449 |
| 4,810,499 | 3/1989 | Nuwayser | 424/448 |
| 4,879,119 | 11/1989 | Konno | 424/449 |
| 4,897,269 | 1/1990 | Mezei | 424/450 |
| 4,900,555 | 2/1990 | Cheng | 424/449 |

FOREIGN PATENT DOCUMENTS 0331391 9/1989 European Pat. Off..

OTHER PUBLICATIONS

Y. W. Cheung, A. Li Wan Po, W. J. Irwin—"Cutaneous Biotransformation as a Parameter in the Modulation of the Activity of Topical Corticosteroids," International Journal of Pharmaceutics, 26, 175–189 (1985).

A. D. Woolfson, D. F. McCafferty and K. E. McGowan, "The Metabolism of Amethocaine by Porcine and Human Skin Extracts: Influence on Percutaneous Anaesthesia," International Journal of Pharmaceutics, 62, 9–14 (1990).

R. O. Potts, S. C. McNeil, C. R. Desbonnet, and E. Wakshull, "Transdermal Drug Transport and Metabolism—The Role of Competing Kinetic Events," Pharmaceutical Research, 6, 119–124 (1989).

*Primary Examiner*—D. Gabrielle Phelan

*Attorney, Agent, or Firm*—Raymond R. Wittekind

[57] ABSTRACT

Novel compositions comprising an antiandrogenic compound of the formula

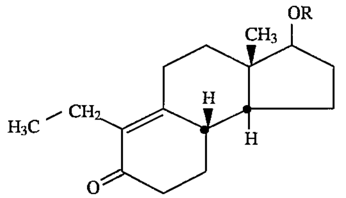

wherein R is $COR_1$ wherein $R_1$ is loweralkyl and a vehicle comprising a metabolism modulator and a polar organic solvent, and a method of controlling the membrane permeation and metabolism of the compound thereof are disclosed.

47 Claims, 4 Drawing Sheets

TRANSDERMAL ANTIANDROGENIC COMPOSITIONS AND MODULATED PROCESS

This is a continuation of application Ser. No. 07/859,745 filed Mar. 30, 1992, now abandoned.

The present invention relates to a composition and a method of controlling membrane permeation and metabolism thereof. More particularly, the present invention relates to a composition comprising an antiandrogenic tricyclic compound of formula 1

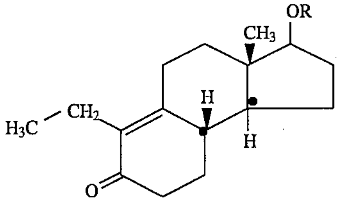
1 wherein R is $COR_1$ wherein $R_1$ is loweralkyl and a vehicle comprising a metabolism modulator and a polar organic solvent, and a method of controlling permeation and metabolism of the tricyclic compound thereof in mammalian skin, mucosa, and other membrane tissue.

The skin, the largest organ of the mammalian body, having a surface area of about two square meters, provides a fertile field for the topical, local, and systemic administration of medicaments. Applied to the skin, medicaments elicit topical effects on the surface and in the horny layer, the stratum corneum, the barrier to skin penetration. Medicaments that surmount this barrier elicit local effects in the epidermis, and those which further penetrate the skin into the dermis enter the microcirculation and eventually the general circulation to elicit systemic effects. Control of the penetration of a medicament into the epidermis or dermis to achieve therapeutic levels of the agent for desired topical or systemic effects, respectively, is generally hindered by the poor diffusion characteristics of most medicaments in the skin and by biotransformations, primarily in the epidermis, leading to metabolites having greater or lesser pharmacological activity, toxicity, or retention properties than the precursor. To improve the diffusion characteristics of medicaments in skin, membrane penetration enhancers such as amides, lactams, and sucrose, and glycerol monofatty acid esters have been employed in admixtures with the medicaments. Such enhancers promote percutaneous transport across the stratum corneum thereby facilitating passage into the viable epidermis/dermis region of the skin. See U.S. Pat. No. 4,808,414 issued Feb. 28, 1989, U.S. Pat. No. 3,969,516 issued Jul. 13, 1976, and U.S. Pat. No. 4,788,062 issued Nov. 29, 1988, respectively, for a discussion of the roles played by amides, lactams, and fatty acid esters as penetration enhancers. Alcohols, such as ethanol, 2-propanol, and the like, have also been used as vehicles for the administration of medicaments to skin to obtain high rates of transport for systemic treatment of various disorders. See U.S. Pat. No. 4,804,541 issued Feb. 14, 1989.

To modulate biotransformations in the skin, particularly enzymatic hydrolysis in the epidermis/dermis regions of the skin, esteruse inhibitors have been utilized. One such inhibitor, diisopropylfluorophosphate, which has been found to efficiently limit enzymatic hydrolysis of medicaments, e.g., salicylate esters in skin, suffers from being highly toxic. See R. O. Potts, et at., Pharmaceutical Research, 6, 119 (1989).

It has now been found that compositions comprising a polar organic solvent and a metabolism modulator provide a vehicle for controlling the rate and extent of membrane permeation and degree of metabolic conversion of topically administered antiandrogenic tricyclic esters of formula 1

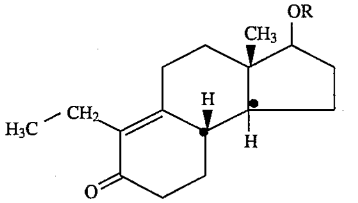
1 wherein R is $COR_1$ wherein $R_1$ is loweralkyl by modulating the metabolic and modifying the transport properties of mammalian skin, mucosa, or other permeable membranes, thereby attaining the objectives of the present invention, namely, to enhance the percutaneous delivery of tricyclic esters 1 (wherein R is $COR_1$ wherein $R_1$ is loweralkyl) through mammalian membranes, to modify the metabolic conversion of tricyclic esters 1 (wherein R is $COR_1$ wherein $R_1$ is loweralkyl) to tricyclic alcohols 1 wherein R is hydrogen (i.e., to control the dermal biotransformation of, e.g., 3β-acetoxy-6-ethyl- 3αβ-methyl- 1,2,3,3a, 4,5,8,9,9a, 9b-decahydro- 7H-benz(e)inden-7-one, inocoterone acetate (wherein R is $COR_1$ wherein $R_1$ is methyl) to the more active metabolite, 6-ethyl-3αβ-methyl- 1,2,3,3a,4,5,8,9,9a, 9b-decahydro-7H-benz(e)inden-3-ol-7-one, inocoterone (wherein R is $COR_1$ wherein $R_1$ is hydrogen), and to regulate the rate of permeation of topically applied tricyclic ester 1 (wherein R is $COR_1$ wherein $R_1$ is loweralkyl) so as to reduce or eliminate systemic effects of the medicament.

As used through the specification and appended claims, the term "alkyl" refers to a straight or branched chain hydrocarbon containing no unsaturation and having 1 to 8 carbon atoms such as methyl, ethyl, 1-, 2-propyl, butyl, 1-pentyl, 3-hexyl, 4-heptyl, 2-octyl, and the like, unless specified otherwise. The term "lower" as applied thereto refers to a group having up to and including 6 carbon atoms.

Control of the rate and extent of membrane penetration and degree of metabolic conversion is achieved by selecting a vehicle comprising the appropriate polar organic solvent and metabolism modulator, and varying the proportion of polar organic solvent and metabolism modulator in the vehicle. Thus, for example, control of the rate and extent of membrane penetration and degree of metabolic conversion is achieved by employing a carbinol of the formula $R_2OH$ wherein $R_2$ is alkyl of 1 to 12 carbon atoms, such as those described above and 1-nonyl, 2-decyl, 3-undecyl, dodecyl, and the like, or alkenyl of 3 to 12 carbon atoms, such as propenyl, 2-butenyl, 2-pentenyl, 2-hexenyl, 3-heptenyl,4-octenyl, 4-nonenyl, 5-decenyl, 5-undecenyl, 6-dodecenyl, and the like, or a ketone of the formula

wherein $R_3$ and $R_4$ are independently alkyl of 1 to 4 carbon atoms, or mixtures thereof, as the polar organic solvent, and an ester of an aliphatic monocarboxylic acid of the formula $R_5CO_2R_6$ wherein $R_5$ and $R_6$ are independently alkyl or alkenyl having a total of 3 to 35 carbon atoms, and mixtures thereof, or a diester of an aliphatic diearboxylic acid of the formula $R_7(CO_2R_6)_2$ wherein $R_6$ is as above and $R_7$ is alkyl or alkenyl having a total of 5 to 46 carbon atoms, or mixtures thereof, or a triester of glycerol of the formula $CH_2OCOR_8$
|
$CH_2OCOR_9$
|
$CH_2OCOR_{10}$ wherein $R_8$, $R_9$ and $R_{10}$ are independently alkyl or alkenyl having a total of 3 to 54 carbon atoms, as the metabolism modulator. Esters of aliphatic monocarboxylic acids include ethyl acetate, cetyl acetate, myristyl acetate, ethyl laurate, propyl burate, butyl laurate, isopropyl myristate, isopropyl palmitate, ethyl oleate, decyl oleate, ethyl linoleate, ethyl linolenate and the like; diesters of aliphatic dicarboxylic acids include dioctyl succinate, dibutyl adipate, dihexyl adipate, dicapryl adipate, diethyl sebacate, diisopropyl sebacate, dibutyl sebacate, dioctyl sebacate, and the like; triesters of glycerol include glyceryl triacetate, glyceryl trilaurate, glyceryl trimyristate, glyceryl tripalmitate, glyceryl trioleate, glyceryl trilinoleate, and the like, as well as triglycerides of coconut oil fatty acids having 8 to 10 carbon atoms, such as Miglyol 810 and Miglyol 812 available from Dynamit Nobel of America, Inc., 105 Stonehurst Court, Northvale, N.J. 07647. Preferred aliphatic monocarboxylic acid esters include isopropyl myristate, ethyl laurate, propyl laurate, butyl laurate, isopropyl palmitate and ethyl oleate, isopropyl myristate being most preferred.

Carbinels include ethanol, 1- and 2-propanol, 1-butariel, 2-pentariel, 3-hexanol, 1-heptanol, 2-octanol, 3-nonanol, 1-deconaol, 1-undodecanol, 1-dodecanol, and the like.

Ketones include acetone, 3-pentanone, 4-heptanone, 5-nonanone, and the like. Ethanol, including 95% ethanol and 2-propanol, and acetone arc the preferred carbinol and ketone, respectively, ethanol being most preferred.

To achieve the objects of the present invention, a trieyclic compound of formula 1 wherein R is $COR_1$ wherein $R_1$ is loweralkyl is dissolved in a vehicle comprising a metabolism modulator and a polar organic solvent, and the composition is applied to mammalian skin, mucusa, or other membrane tissue. The metabolism modulator is generally present in the mount of about 0.5 to about 99.5% by weight of the vehicle, the mount of polar solvent, by necessary, being from about 99.5 to 0.5% by weight of the vehicle. While the amounts of metabolism modulator and polar solvent are not narrowly critical within the aforementioned ranges, the presence of both modulator and solvent is necessary to achieve the stated objectives. The amount of antiandrogcnic tricyclie ester 1 wherein R is $COR_1$ wherein $R_1$ is loweralkyl admixed with the vehicle is such that the desired pharmacological effect, andandrogenic activity, is achieved over the desired time period. Generally, the amount of ester 1 wherein R is $COR_1$ wherein $R_1$ is loweralkyl admixed with the vehicle falls within the range of from about 0. 1 to about 40% by total weight of the vehicle, most preferably about 0.5 to about 20% by total weight of the vehicle.

BRIEF DESCRIPTION OF THE DRAWINGS

FIGS. 1, 2 and 3 graphically depict the results of the experiments described in Examples 1, 2 and 3, respectively.

Figure 1:
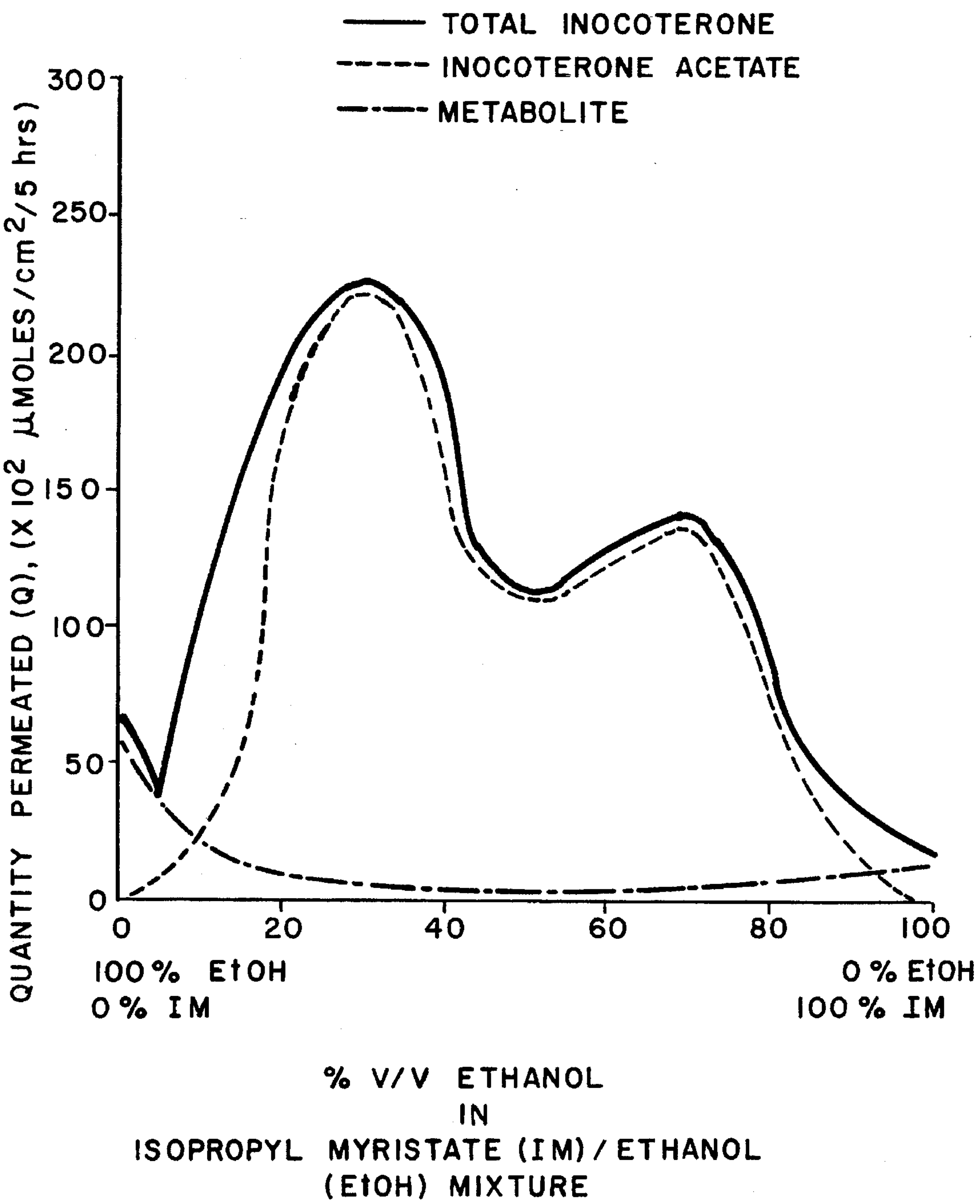
In FIGS. 1, 2 and 3, the amount of inocoterone acetate and its metabolite, as well as the summation thereof, the total inocoterone, permeated through a specified area of skin over a specified period of time is plotted against the concentration of the metabolism modulator, isopropyl myristate, in ethanol, acetone and isopropanol, respectively, to show the change in the permeation of the medicament with change in the amount of modulator in the organic solvent system.

The compositions of the present invention maybe applied directly to membrane tissue or may be incorporated into a solution, suspension, ointment, cream, lotion, gel, or plastic, using conventional inert excipients (carriers). These pharmaceutical compositions should contain at least 0.1% of the active composition; the amount may vary, however, between about 0.1% and about 20% of the weight thereof. The amount of active composition in the pharmaceutical formulation is such that a suitable dosage is obtained. For the formulation of solutions the compositions of the present invention may be dissolved in glycerin, propylene glycol, polyethylene glycols, or other synthetic solvents, and the solution may be applied directly to the skin, or adsorbed onto a cotton pad, sterile gauze, or porous membrane and applied topically. The suspensions, creams, lotions, and gels may contain emulsifying and/or solubilizing agents such as acacia, glyceryl monostearate, lecithin, Poloxamer brand of polyoxyethylene, polyoxypropylene block polymer available from BASF Wyandotte Corporation, 1609 Biddle Avenue, Wyandotte, Mich. 48192, polysorbates, Spans brand of sorbitan mono- and tri-fatty acid esters available from ICI America Inc., Wilmington, Del. 19899, and the like, and suspending and/or viscosity-increasing agents such as agar, alginic acid, aluminum monostearate, Carbopol 940 or Carbomer 934P brand of polyacrylic acid available from B. F. Goodrich Chemical Co., 6100 Oak Tree Blvd., Cleveland, Ohio 04431, sodium carboxymethylcellulose, carrageenan, dextrin, gelatin, hydroxypropyl cellulose, hydroxypropyl methylcellulose, hydroxethyl cellulose, methylcellulose, pectin, polyethylene oxide, Povidone brand of polyvinylpyrrolidone available from GAF Corporation, 1361 Alps Road, Wayne, N.J. 07470, propylene glycol alginate, tragacanth and the like, and ointment bases such as lanolin, polyethylene glycol, petrolatom, squarene and the like, and humectants such as glycerin, propylene glycol, sorbitol and the like, in an amount of about 1 to about 10% by of the formulation.

The antiandrogenic compounds of the compositions of the present invention as prepared by the processes described in U.S. Pat. Nos. 4,466,971, 4,607,054, and 4,849,454, issued Aug. 21, 1984, Aug. 19, 1986, and Jul. 18, 1989, and are reported to be useful for the treatment of acne, hirsutism, seborrhea, among other, affiliations due to hyperandrogenicity.

The invention is further illustrated by the following examples which are illustrative of a specific mode of practicing the invention and is not intended as limiting the scope of the appended claims.

EXAMPLE 1

In Vitro Skin Permeation and Metabolism Studies

The freshly excised hairless mouse skin was used in the two-compartment diffusion cell method of Chlen et at., *Drug Development and Industrial Pharmacy*, 11, 1333–1173 (1985). The hairless mouse (HRS/J strain) was sacrificed just prior to the experiment by cervical dislocation. A square section of the abdominal skin was surgically removed and mounted between two side-by-side half cells; the exposed area of the skin being approximately 0.64 $cm^2$. A 1–10% weight/volume (w/v) solution of inocoterone acetate and vehicle was added to the donor compartment and a 40% w/v polyethylene glycol 400/normal saline solution was added to the receptor compartment. Simultaneous skin permeation and biotransformation studies Were conducted in a thermostated diffusion cell apparatus at 37° C. At appropriate intervals samples were withdrawn from the receptor compartment and analyzed for inocoterone acetate and its metabolite, inocoterone, by high pressure liquid chromatography. No significant hydrolysis of the inocoterone acetate in the blank receptor solution was noted during the time course of the permeation experiment. Each experiment was carried out in at least triplicate. This method was used in Examples 3 to 6.

For the evaluation of pharmaceutical compositions of the present invention, the freshly excised hairless mouse skin was used in the diffusion cell method of Franz, *Current Problems in Dermatology,* 7, 58–68 (1978), in a vertical position, the exposed area of the skin being approximately 1.8 $cm^2$. The pharmaceutical formulation of known concentration in vehicle was added to the upper compartment of the cell, which was exposed to the stratum corneum side of the skin, and a 40% polyethylene glycol 400/normal saline solution was placed in the lower compartment The penetration and metabolism rates were studied in a thermostated diffusion cell at 37° C. using the analytical method described above. Each experiment was carried out in at least triplicate. This method was used in Examples 7 and 13.

EXAMPLE 2

In Vivo Antiandrogen Activity Test—Rat

Male rats (intact or castrated) were treated topically with specified doses of inocoterone acetate solution in various solvent systems on days 1, 2, 3, 6 and 7 of each week for 1 to 3 weeks. The castrated rats received daily injections of testosterone propionate (250 μg/day) subcutaneously. One day after the last administration, the animals were sacrificed and fragments of the skin and prostates were removed. The skin fragments were prepared for quantitative measurement of volume density of smooth endoplasmic reficulum (SER) by means of electron microscopy and the prostates were weighed. The studies using intact rats and castrated rats stimulated with testosterone propionate demonstrated a dose related reduction in volume density of SER with inocoteione acetate at a dose image from 0.25 to 25 mg/rat/day, whereas there was no significant effect on prostate weight at any dose.

EXAMPLE 3

Compositions of 10% w/v of inocoterone acetate in vehicle solutions were prepared by dissolving 1 g of the medicament in 10 ml of a mixture of isopropyl myristate and 95% ethanol in the following volume percent ratios: 100:0, 95:5, 70:30, 60:40, 50:50, 40:60, 30:70, 5:95 and 0:100, respectively. The in vitro skin permeation and metabolism rates were measured using the method described under the in vitro skin permeation test method. The results of these measurements, in terms of the cumulative mount of unchanged medicament and its metabolite permeated in μmoles per square centimeter with time, over 5 hours are given in FIG. 1.

Figure 2:
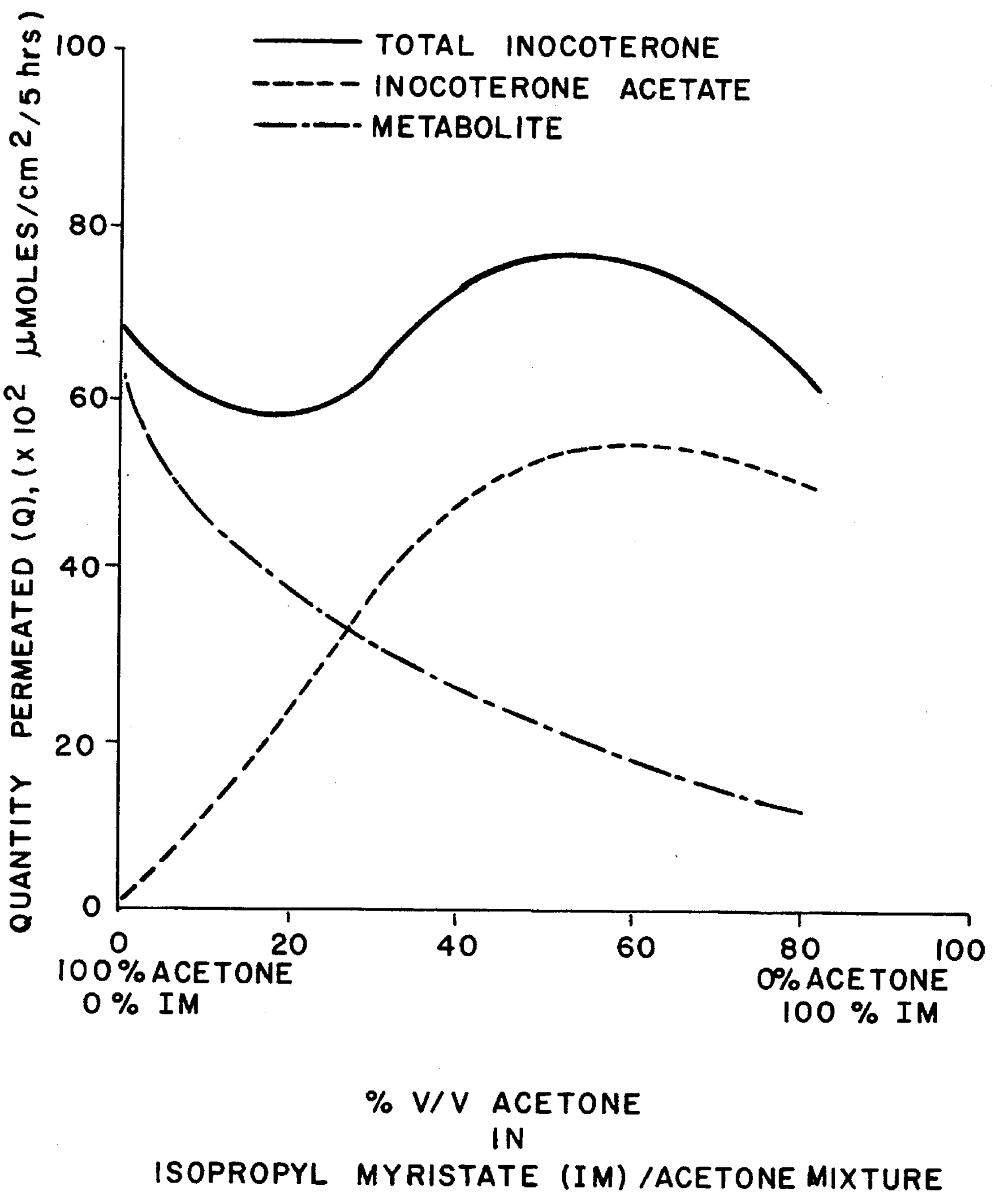

The procedure of Example 3 was repeated except that the mixtures comprised isopropyl myristate and acetone in the following volume percent ratios: 100:0, 80:20, 50:50 and 20:80, respectively. The simultaneous skin permeation and metabolism rates generated from these medicament solutions using the method described in Example 1 are given in FIG. 2.

EXAMPLE 4

Figure 3:
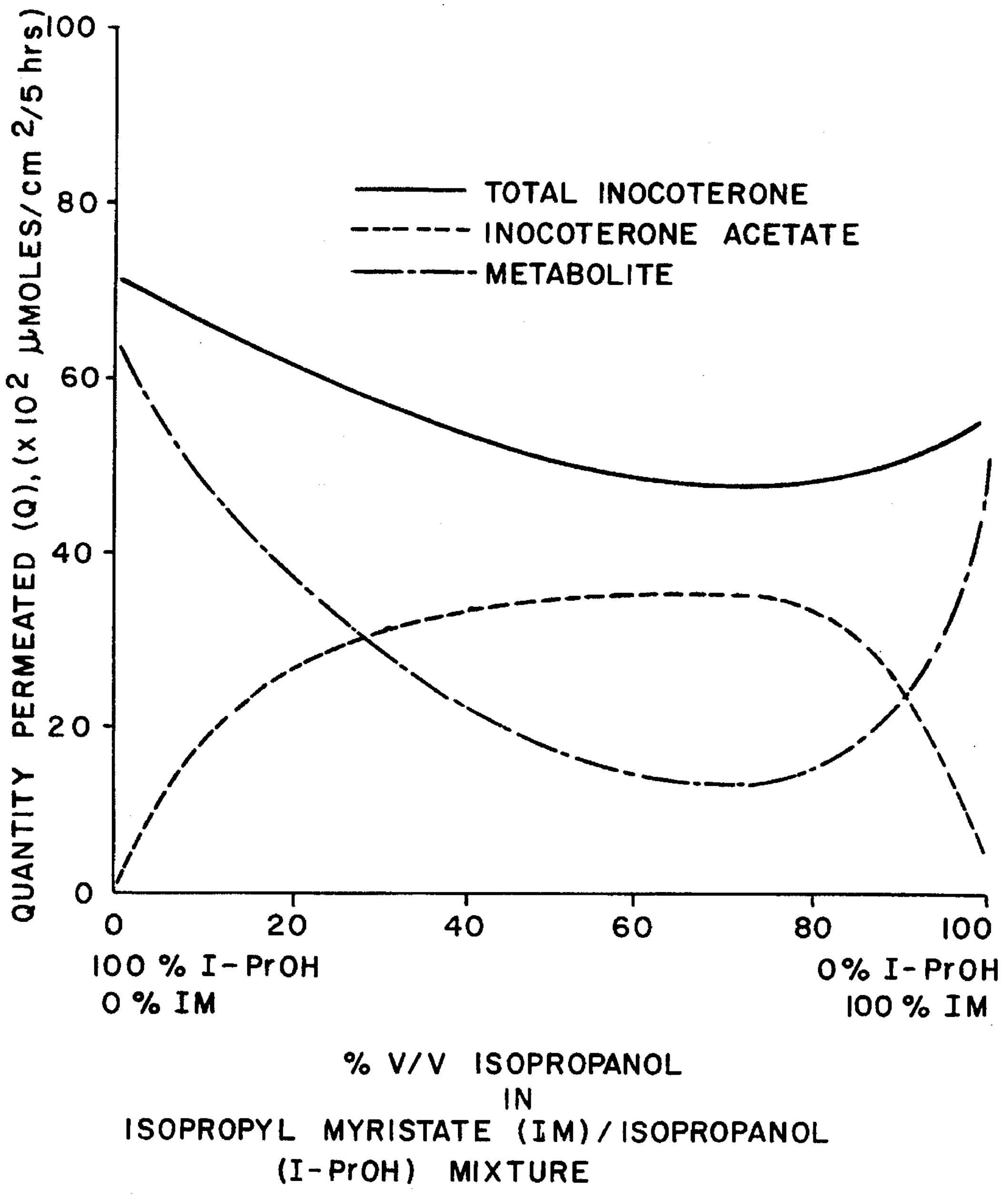

The procedure of Example 3 was repeated except that the mixtures comprised isopropyl myristate and isopropyl alcohol in the following volume percent ratios: 100:0, 80:20, 50:50, 20:80 and 0:100, respectively. The simultaneous skin permeation and metabolism rates generated from these medicament solutions using the method described under Example 1 are given in FIG. 3.

EXAMPLE 5

Figure 4:
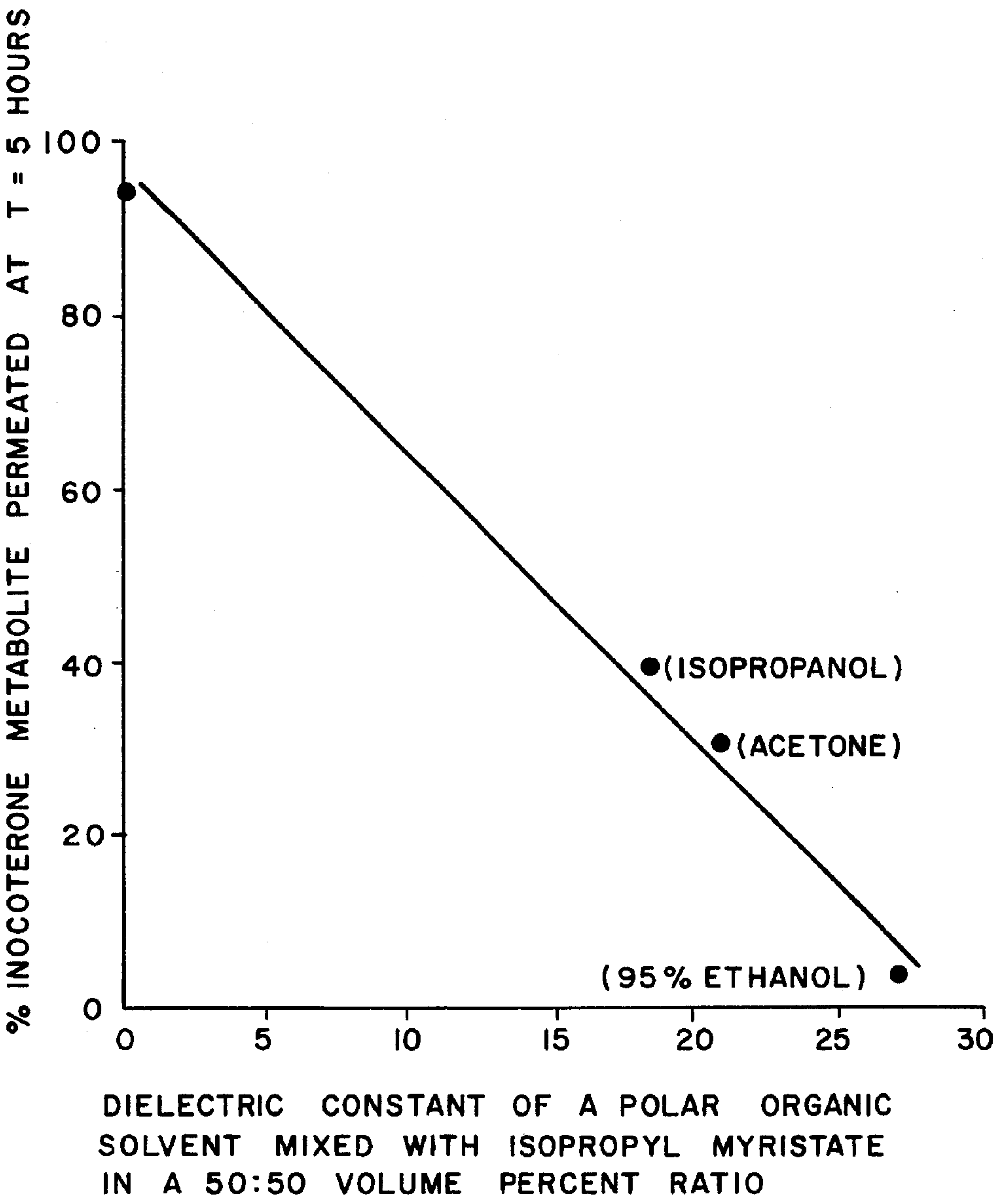
In FIG. 4, the permeation of inocoterone metabolite is plotted against the dielectric constant of the organic solvent mixed with the metabolism modulator, isopropyl myristate, to show the change in skin permeation with the change of the dielectric constant of the medium.

In this example, isopropyl myristate is used as a metabolism modulator in combination with a polar organic solvent having various polarities (dielectric constants) in a 50:50 volume percent ratio for the evaluation of the skin permeation and metabolism rates of inocoterone acetate. The relationship between the percent metabolite determined based on the total medicament permeated in the first 5 hour time period and the dielectric constant of the polar organic of in the solvent mixtures is given in FIG. 4.

EXAMPLE 6

In this example, the results of the use of ethanol as the polar organic solvent in combination with various fatty acid esters for the simultaneous skin permeation and metabolism of inocoterone acetate solution are shown.

| | Transdermal Flux $Q_1$ (× $10^2$ μmoles/$cm^2$/5 hrs) | | | |
|---|---|---|---|---|
| Vehicle | Inocoterone Acetate | Inocoterone | Total Inocoterone | % Metabolite |
| Ethanol | 0 | 1.1 | 1.1 | 100.0 |
| 10% Ethyl laurate-90% Ethanol | 28.1 | 58.3 | 86.4 | 67.5 |
| 10% Propyl laurate-90% Ethanol | 25.8 | 60.8 | 86.6 | 70.2 |
| 10% Butyl laurate-90% Ethanol | 39.9 | 54.5 | 94.4 | 57.7 |
| 10% Isopropyl palmitate- | 9.4 | 27.5 | 36.9 | 74.5 |

-continued

| Vehicle | Transdermal Flux $Q_1$ (× $10^2$ μmoles/$cm^2$/5 hrs) Inocoterone Acetate | Inocoterone | Total Inocoterone | % Metabolite |
|---|---|---|---|---|
| 90% Ethanol 10% Ethyl oleate-90% Ethanol | 18.5 | 36.6 | 55.1 | 66.4 |

EXAMPLE 7

A composition, in the form of a gel, suitable for topical application of inocoterone acetate is prepared by mixing the following components in the given concentrations.

| Component | Weight % |
|---|---|
| Inocoterone acetate | 1–10 |
| Butyl laurate | 5–20 |
| Ethanol | 10–50 |
| Polyacrylic acid (Carbopol 940) | 0.5–2 |
| Triethanolamine (neutralizing agent) | q.s. |
| Sorbic acid (preservative) | q.s. |
| Deionized water | q.s. to 100 |

EXAMPLE 8

Ethyl laurate, propyl laurate, isopropyl myristate, isopropyl palmitate, dioctyl sebacate, ethyl oleate, isopropyl laurate, diisopropyl sebacate, and the like, may be substituted for butyl laurate in Example 7, to provide a topical composition suitable for the topical delivery of inocoterone acetate.

EXAMPLE 9

A polar organic solvent, e.g., n-propanol or isopropanol, is substituted for ethanol in Example 7, to provide a topical composition suitable for the topical delivery of inocoterone acetate.

EXAMPLE 10

A neutralizing agent, e.g., triethylene amine, sodium hydroxide or Ethomeen C/25 brand of polyethylene glycol amine of coconut acid available from Akzo Chemical Co., 8201 West 471h Street, McCook, Ill. 60525, may be substituted for triethanolamine in Example 7, to provide a topical gel preparation suitable for the percutaneous delivery of inocoterone acetate.

EXAMPLE 11

A pharmaceutical composition in the form of a cellulose gel is prepared by mixing is following components in the following given concentrations:

| Component | Weight % |
|---|---|
| Inocoterone acetate | 1–10 |
| Butyl laurate | 10–50 |
| Ethanol | 5–20 |
| Sorbic acid (preservative) | q.s. |
| Hydroxypropyl cellulose | 1–5 |
| Deionized water | q.s. to 100 |

EXAMPLE 12

A cellulose-type gelling agent, e.g., hydroxypropyl methylcellulose, hydroxyethyl cellulose, or sodium carboxymethyl cellulose may be substituted for hydroxypropyl cellulose of Example 11 to provide a topical composition suitable for the dermal delivery of inocoterone acetate.

EXAMPLE 13

In this example the simultaneous skin permeation and metabolism rates of inocoterone acetate incorporated in the Carbopol 940 gels formulated using the compositions described in Example 7 are shown.

| Composition | Percent w/w | Transdermal Flux $Q_1$ (× $10^2$ μmoles/$cm^2$/5 hours Inocoterone Acetate | Inocoterone | Total Inocoterone | % Metabolite |
|---|---|---|---|---|---|
| Inocoterone acetate | 10.0 | 36.2 | 62.8 | 99.0 | 63.4 |
| Isopropyl myristate | 6.0 | | | | |
| Ethanol | 50.0 | | | | |
| Carbopol 940 | 0.7 | | | | |
| Triethanolamine | 0.3 | | | | |
| Deionized water | 33.0 | | | | |
| Inocoterone acetate | 10.0 | 38.4 | 52.7 | 91.1 | 57.8 |
| Ethyl laurate | 6.0 | | | | |
| Ethanol | 50.0 | | | | |
| Carbopol 940 | 0.7 | | | | |

-continued

| | | Transdermal Flux $Q_1$ (× $10^2$ μmoles/$cm^2$/5 hours | | | |
|---|---|---|---|---|---|
| Composition | Percent w/w | Inocoterone Acetate | Inocoterone | Total Inocoterone | % Metabolite |
| Triethanolamine | 0.3 | | | | |
| Deionized water | 33.0 | | | | |
| Inocoterone acetate | 10.0 | 45.2 | 66.2 | 111.4 | 59.4 |
| Butyl laurate | 6.0 | | | | |
| Ethanol | 50.0 | | | | |
| Carbopol 940 | 0.7 | | | | |
| Triethanolamine | 0.3 | | | | |
| Dionized water | 33.0 | | | | |

EXAMPLE 14

In this example, the comparative effect of the vehicle systems of ethanol and a a 40% isopropyl myristate-60% ethanol mixture on the in vivo efficacy of inocoterone acetate on the rat sebaceous gland is shown. The medicament in a dose of 0.5 mg/$cm^2$/day for 5 days in 5 $cm^2$ area was applied to the skin of testosterone propionate-treated castrated rats using the solvent systems described above. From the isopropyl myristate-ethanol system, inocoterone acetate completely inhibited the testosterone-induced increase in the volume density of the smooth endoplasmic reticulum vesicles in the intermediate cells on the rat sebaceous gland. When the same dose of inocoterone acetate was applied using ethanol as the solvent, the effects of testosterone on the sebaceous gland were inhibited by 60%. Topical administration of the medicament with the isopropyl myristate-ethanol mixture resulted in a systemic anfiandrogenic effect as evidenced by changes in the prostate.

The greater efficacy of inocoterone acetate when applied in the isopropyl myristate-ethanol mixture is consistent with the increased transcutaneous penetration observed in Example 3.

We claim:

1. A composition consisting essentially of an antiandrogenic tricyclic compound of the formula

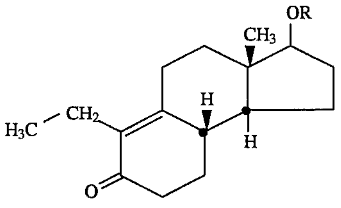

wherein R is $COR_1$ wherein $R_1$ is loweralkyl of 1 to 6 carbon atoms, a metabolism modulator selected from the group consisting of a compound of the formula $R_5CO_2R_6$ wherein $R_5$ and $R_6$ are independently alkyl or alkenyl having a total of 3 to 35 carbon atoms, a compound of the formula $R_7(CO_2R_6)_2$ wherein $R_6$ is as defined above and $R_7$ is alkyl or alkenyl having a total of 5 to 46 atoms, and a compound of the formula

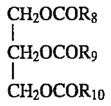

wherein $R_8$, $R_9$, and $R_{10}$ are independently alkyl or alkenyl having a total of 3 to 54 carbon atoms; or mixtures thereof, and a polar organic solvent selected from the group consisting of a compound of the formula $R_2OH$ wherein $R_2$ is alkyl of 2 to 12 carbon atoms or alkenyl of 3 to 12 carbon atoms; or a compound of the formula

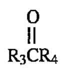

wherein $R_3$ and $R_4$ are independently alkyl of 1 to 6 carbon atoms, or mixtures thereof.

2. A compound according to claim 1 wherein $R_1$ is methyl.

3. A composition according to claim 1 wherein the metabolism modulator is a compound of the formula $R_5CO_2R_6$.

4. A composition according to claim 1 wherein the metabolism modulator is a compound of the formula $R_7(CO_2R_6)_2$.

5. A composition according to claim 1 wherein the metabolism modulator is a compound of the formula

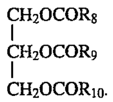

6. A composition according to claim 3 wherein the compound is selected from group consisting of ethyl acetate, cetyl acetate, ethyl laurate, myristyl acetate, ethyl propyl laurate, butyl laurate, isopropyl myristate, isopropyl palmitate, ethyl oleate, oleate, ethyl linoleate, and ethyl linolenate.

7. A composition according to claim 6 wherein the compound is selected from the group consisting of isopropyl myristate, ethyl laurate, propyl laurate, butyl laurate, isopropyl palmitate, and ethyl oleate.

8. The composition according to claim 7 wherein the metabolism modulator is isopropyl myristate.

9. A composition according to claim 4 wherein the compound is selected from the group consisting of dioctyl succinate, dibutyl adipate, dihexyl adipate, dicapryl adipate, diethyl sebacate, diisopropoyl sebacate, dibutyl sebacate, and dioctyl sebacate.

10. A composition according to claim 5 wherein the compound is selected from the group consisting of triglycerides of 8 carbon atoms coconut oil fatty acids and triglycerides of 10 carbon atoms coconut oil fatty acids.

11. A composition according to claim 1 wherein the polar organic solvent is a compound of the formula $R_2OH$.

12. A composition according to claim 1 wherein the polar organic solvent is a compound of the formula

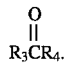

13. The composition according to claim 11 wherein the polar organic solvent is ethanol.

14. The composition according to claim 11 wherein the polar organic solvent is 2-propanol.

15. The composition according to claim 12 wherein the polar organic solvent is acetone.

16. A composition according to claim 1 wherein the weight percent of the metabolism modulator is from about 0.5 to about 99.5% of the vehicle.

17. A composition according to claim 1 wherein the weight percent of the tricyclic compound is about 0. 1 to about 40% of the vehicle.

18. A composition according to claim 17 wherein the weight percent of the tricyclic compound is about 0.5 to about 20% of the vehicle.

19. A pharmaceutical composition consisting essentially of an antiandrogenic tricyclic compound of the formula

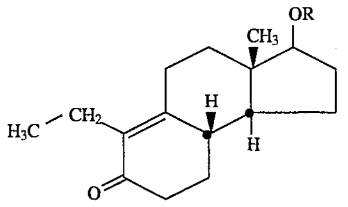

wherein R is $COR_1$ wherein $R_1$ is loweralkyl of 1 to 6 carbon atoms, a metabolism modulator selected from the group consisting of a compound of the formula $R_5CO_2R_6$ wherein $R_5$ and $R_6$ are independently alkyl or alkenyl having a total of 3 to 35 carbon atoms, a compound of the formula $R_7(CO_2R_6)_2$ wherein $R_6$ is as defined above and $R_7$ is alkyl or alkenyl having a total of 5 to 46 atoms, and a compound of the formula

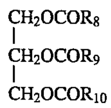

wherein $R_8$, $R_9$, and $R_{10}$ are independently alkyl or alkenyl having a total of 3 to 54 carbon atoms; or mixtures thereof, and a polar organic solvent selected from the group consisting of a compound of the formula $R_2OH$ wherein $R_2$ is alkyl of 2 to 12 carbon atoms or alkenyl of 3 to 12 carbon atoms; or a compound of the formula

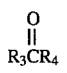

wherein $R_3$ and $R_4$ are independently alkyl of 1 to 6 carbon atoms, or mixtures thereof and as a carrier therefor a solution, suspension, ointment, cream, lotion, plastic or gelling agent.

20. A pharmaceutical composition according to claim 19 wherein the gelling agent is a cellulose, a polyacrylic acid, or a lecithin.

21. The pharmaceutical composition according to claim 20 wherein the gelling agent is polyacrylic acid.

22. The pharmaceutical composition according to claim 21 wherein the gelling agent is carboxypolymethylene.

23. The pharmaceutical composition according to claim 20 wherein the gelling agent is an alkyl cellulose.

24. A pharmaceutical composition according to claim 23 wherein the alkyl cellulose is selected from the group consisting of hydroxypropyl methylcellulose, hydroxypropyl cellulose, and sodium carboxymethyl cellulose.

25. The pharmaceutical composition according to claim 24 wherein the alkyl cellulose is hydroxyethyl cellulose.

26. The pharmaceutical composition according to claim 20 wherein the gelling agent is lecithin.

27. The pharmaceutical composition according to claim 20 wherein the weight of the gelling agent is from about 1 to about 5%.

28. The pharmaceutical composition according to claim 27 wherein the weight the gelling agent is from about 1 to 5%.

29. The pharmaceutical composition according to claim 28 wherein the weight percent of the gelling agent is from about 0.5 to about 2.0%.

30. A method of controlling the rate and degree of permeation in mammalian skin, mucosa, or other permeable membrane of a tricyclic compound of the formula

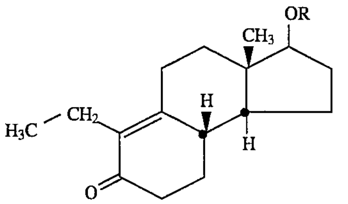

wherein R is $COR_1$ wherein $R_1$ is loweralkyl of 1 to 6 carbon atoms, which comprises application to the skin, mucosa or other permeable membrane a composition consisting essentially of an antiandrogenic tricyclic compound of the formula

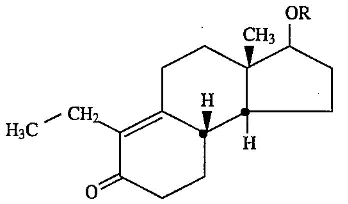

wherein R is $COR_1$ wherein $R_1$ is loweralkyl of 1 to 6 carbon atoms, a metabolism modulator selected from the group consisting of a compound of the formula $R_5CO_2R_6$ wherein $R_5$ and $R_6$ are independently alkyl or alkenyl having a total of 3 to 35 carbon atoms, a compound of the formula $R_7(CO_2R_6)_2$ wherein $R_6$ is as defined above and $R_7$ is alkyl or alkenyl having a total of 5 to 46 atoms, and a compound of the formula

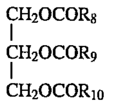

wherein $R_8$, $R_9$, and $R_{10}$ are independently, alkyl or alkenyl having a total of 3 to 54 carbon atoms; or mixtures thereof, and a polar organic solvent selected from the group consisting of a compound of the formula $R_2OH$ wherein $R_2$ is alkyl of 2 to 12 carbon atoms or alkenyl of 3 to 12 carbon atoms; or a compound of the formula

O
||
$R_3CR_4$ wherein $R_3$ and $R_4$ are independently alkyl of 1 to 6 carbon atoms, or mixtures thereof.

31. A method according to claim 30 wherein $R_1$ is methyl.

32. A method according to claim 30 wherein the metabolism modulator is a compound of the formula $R_5CO_2R_6$.

33. A method according to claim 30 wherein the metabolism modulator is a compound of the formula $R_7(CO_2R_6)_2$.

34. A method according to claim 30 wherein the metabolism modulator is a compound of the formula $CH_2OCOR_8$
|
$CH_2OCOR_9$
|
$CH_2OCOR_{10}$.

35. A method according to claim 32 wherein the compound is selected from the group consisting of ethyl acetate, cetyl acetate, ethyl laurate, myristyl acetate, propyl laurate, butyl burate, isopropyl myristate, isopropyl palmitate, ethyl oleate, decyl oleate, ethyl linoleate, and ethyl linolenate.

36. A composition according to claim 35 wherein the compound is selected from the group consisting of isopropyl myristate, ethyl laurate, propyl laurate, butyl laurate, isopropyl palmitate, and ethyl oleate.

37. The method according to claim 36 wherein the metabolism modulator is isopropyl myristate.

38. A method according to claim 33 wherein the compound is selected from the group consisting of dioctyl succinate, dibutyl adipate, dihexyl adipate, dicapryl adipate, diethyl sebacate, diisopropyl sebacate, dibutyl sebacate, and dioctyl sebacate.

39. A method according to claim 34 wherein the compound is selected from the group consisting of triglycerides of 8 carbon atoms coconut oil fatty acids and triglycerides of 10 carbon atoms coconut oil fatty acids.

40. A method according to claim 30 wherein the polar organic solvent a compound of the formula $R_2OH$.

41. A method according to claim 30 wherein the polar organic solvent is a compound of the formula

O
||
$R_3CR_4$.

42. The method according to claim 35 wherein in the polar organic solvent is ethanol.

43. The method according to claim 37 wherein the polar organic solvent is 2-propanol.

44. The method according to claim 41 wherein the polar organic solvent is acetone.

45. A method according to claim 30 wherein the weight percent of the metabolism modulator is from about 0.5 to about 99.5% of the vehicle.

46. A method according to claim 30 wherein the weight percent of the tricyclic compound is about 0.1 to about 40% of the vehicle.

47. A method according to claim 38 wherein the weight percent of the tricyclic compound is about 0.5 to about 20% of the vehicle.

* * * * *